(12) United States Patent
Watanabe

(10) Patent No.: US 9,271,635 B2
(45) Date of Patent: Mar. 1, 2016

(54) FLUORESCENCE ENDOSCOPE APPARATUS

(71) Applicant: OLYMPUS CORPORATION, Tokyo (JP)

(72) Inventor: Toshiaki Watanabe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 267 days.

(21) Appl. No.: 13/908,116

(22) Filed: Jun. 3, 2013

(65) Prior Publication Data

US 2013/0338438 A1 Dec. 19, 2013

(30) Foreign Application Priority Data

Jun. 4, 2012 (JP) .................................. 2012-126814

(51) Int. Cl.
| | | |
|---|---|---|
| A61B 1/06 | (2006.01) | |
| A61B 1/04 | (2006.01) | |
| A61B 1/00 | (2006.01) | |

(52) U.S. Cl.
CPC ............. *A61B 1/043* (2013.01); *A61B 1/0002* (2013.01); *A61B 1/00009* (2013.01); *A61B 1/00045* (2013.01); *A61B 1/0638* (2013.01); *A61B 1/0646* (2013.01); *A61B 1/0684* (2013.01)

(58) Field of Classification Search
CPC ............. A61B 1/00009; A61B 5/0071; A61B 5/14556
See application file for complete search history.

(56) References Cited

U.S. PATENT DOCUMENTS

| | | | | |
|---|---|---|---|---|
| 6,069,689 A * | 5/2000 | Zeng | ................... | A61B 5/0059 356/301 |
| 6,293,911 B1 * | 9/2001 | Imaizumi | ........... | A61B 1/00009 600/160 |
| 6,537,211 B1 * | 3/2003 | Wang | ................. | A61B 1/00009 600/160 |
| 7,179,222 B2 * | 2/2007 | Imaizumi | ........... | A61B 1/00009 600/109 |
| 7,420,151 B2 * | 9/2008 | Fengler | .............. | A61B 1/00009 250/208.1 |
| 8,300,093 B2 * | 10/2012 | Ayame | ............... | A61B 1/00009 348/71 |
| 8,498,695 B2 * | 7/2013 | Westwick | .............. | A61B 1/045 600/109 |
| 9,044,163 B2 * | 6/2015 | Yamaguchi | .......... | A61B 1/0638 |
| 2002/0138008 A1 * | 9/2002 | Tsujita | ............... | A61B 1/00009 600/473 |
| 2002/0161282 A1 * | 10/2002 | Fulghum | ............ | A61B 1/00009 600/160 |
| 2003/0191368 A1 * | 10/2003 | Wang | ................. | A61B 1/00009 600/160 |
| 2005/0288593 A1 * | 12/2005 | Georgakoudi | ....... | A61B 5/0059 600/476 |

(Continued)

FOREIGN PATENT DOCUMENTS

JP 2011-188929 A 9/2011

*Primary Examiner* — Anhtuan T Nguyen
*Assistant Examiner* — Jae Woo
(74) *Attorney, Agent, or Firm* — Scully, Scott, Murphy & Presser, P.C.

(57) ABSTRACT

A fluorescence endoscope apparatus includes: a light source unit emitting light in a combination of light in plural types of wavelength bands in two types of wavelength ranges of RGB and two types of exciting light, with plural types of emitting patterns and in a time division; an image pickup unit receiving reflected light and two types of fluorescence; and an image-processing unit outputting a white light image and two types of fluorescence images.

9 Claims, 10 Drawing Sheets

(56) References Cited

U.S. PATENT DOCUMENTS

| | | | | |
|---|---|---|---|---|
| 2006/0020169 A1* | 1/2006 | Sugimoto | A61B 1/00009 | 600/180 |
| 2006/0173240 A1* | 8/2006 | Fukuyama | A61B 1/00039 | 600/118 |
| 2006/0247537 A1* | 11/2006 | Matsumoto | A61B 1/00009 | 600/478 |
| 2007/0121786 A1* | 5/2007 | Okawa | A61B 1/24 | 378/119 |
| 2008/0239070 A1* | 10/2008 | Westwick | A61B 1/045 | 348/68 |
| 2009/0156901 A1* | 6/2009 | Gono | A61B 1/0646 | 600/180 |
| 2009/0289200 A1* | 11/2009 | Ishii | A61B 1/00009 | 250/459.1 |
| 2011/0235324 A1* | 9/2011 | Irion | A61B 1/0638 | 362/235 |
| 2013/0150728 A1* | 6/2013 | Takei | A61B 6/52 | 600/476 |
| 2014/0005476 A1* | 1/2014 | Matsumoto | A61B 1/00009 | 600/109 |
| 2015/0022647 A1* | 1/2015 | Takei | A61B 1/00186 | 348/70 |

* cited by examiner

TIMING CHART FOR IMAGE ACQUISITION (FRAME SEQUENTIAL METHOD, FLUORESCENCE 1~FLUORESCENCE n, WHITE LIGHT)

LIGHT ABSORPTION PROPERTY
OF OXYHEMOGLOBIN

B
400nm~470nm

G
470nm~580nm

R
580nm~600nm

R
600nm~700nm

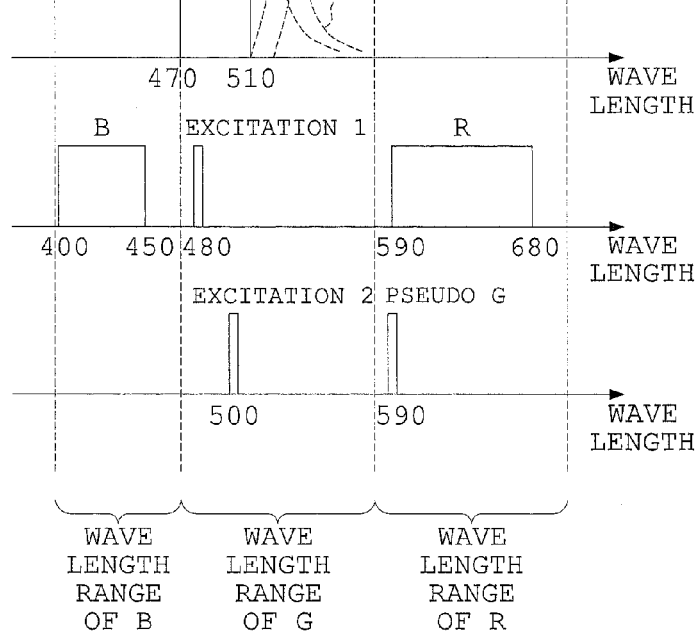

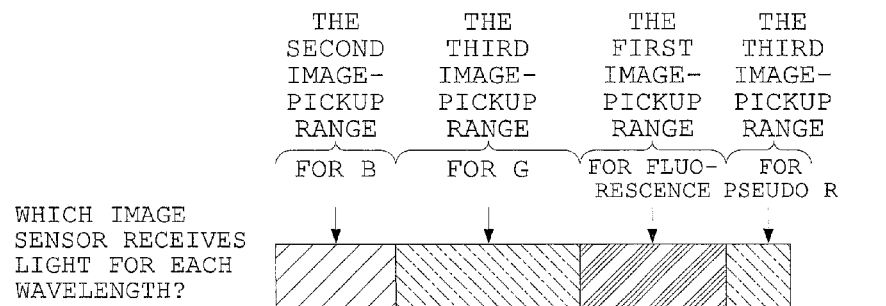
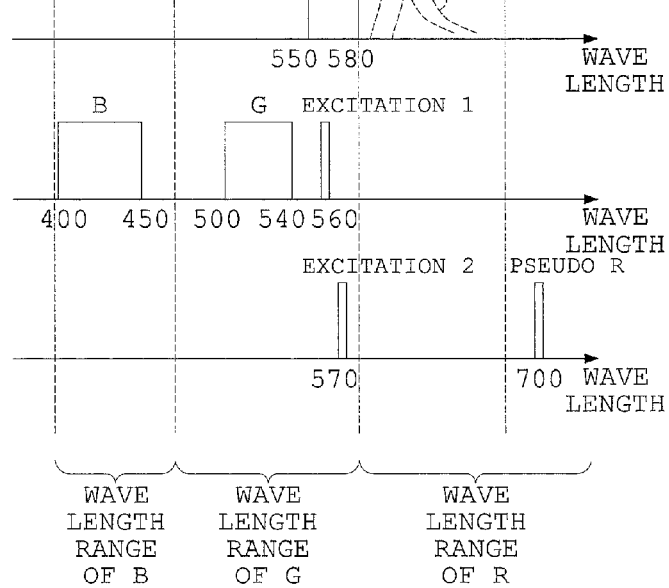

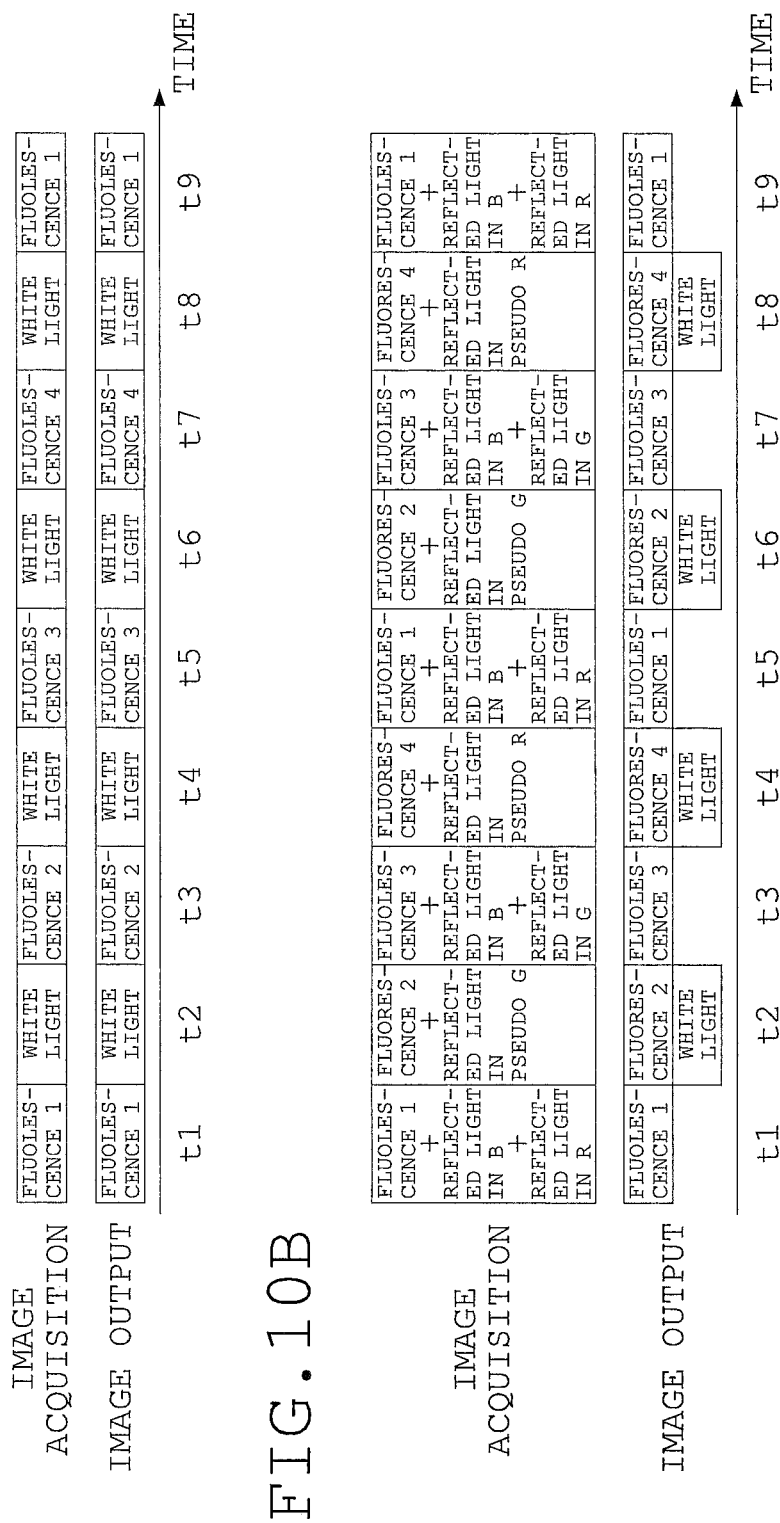

FLUORESCENCE ENDOSCOPE APPARATUS

This application claims benefits of Japanese Patent Application No. 2012-126814 filed in Japan on Jun. 4, 2012, the contents of which are incorporated herein by reference.

BACKGROUND THE INVENTION

1. Field of the Invention

This invention relates to a florescence endoscope apparatus for capturing: a white light image that is used for acquiring information on the shape of an object to be observed, like a living body for example; and plural types of fluorescence images that are used for acquiring information on a degenerate site of the object to be observed, such as a lesion in a living body.

2. Description of Related Art

As a conventional fluorescence endoscope apparatus for capturing plural types of fluorescence images and a white light image while a decrease in a frame rate for white light image showing information on shape with one observation mode is being controlled to the small extent to the utmost, a fluorescence endoscope apparatus disclosed in Japanese Patent Kokai No. 2011-188929 has been suggested for example.

FIGS. 1A-1C are explanatory views showing one example of structures for the fluorescence endoscope apparatus disclosed in Japanese Patent Kokai No. 2011-188929. To be specific, FIG. 1A is a block diagram conceptually showing its whole structure, FIG. 1B is a view showing a configuration of respective transmittal portions of a rotary filter that is provided for a light source unit for the apparatus shown in FIG. 1A, and FIG. 1C is a timing chart conceptually showing timing with which a white light image and plural types of fluorescence images are captured in the fluorescence endoscope apparatus disclosed in Japanese Patent Kokai No. 2011-188929.

The fluorescence endoscope apparatus shown in FIGS. 1A-1C include a light source unit 51, an image pickup unit 52, and an image processing unit 54. In FIG. 1A, the numeral reference 53 denotes a light-guiding means like a light guide, the numeral reference 54a denotes a frame memory, the numeral reference 55 denotes an image-displaying apparatus, and the numeral reference 56 denotes an insertion unit of the front end of the endoscope.

The light source unit 51 includes a light source 51a and a rotary filter 51b. The light source 51a emits light containing: white light for observing the shape of an object 59 to be observed; and plural types of exciting light for exciting plural types of fluorescent substances that exist in the object 59. The rotary filter 51b is provided with: white light-transmitting portions 51b2 and 51b4 that transmit white light of light emitting from the light source 51a; and plural types of exciting light-transmitting portions 51b1 and 51b3 that transmit plural types of exciting light respectively of light emitting from the light source 51a, with these transmittal portions 51b1, 51b2, 51b3, and 51b4 located in the same circumferential direction.

The image pickup unit 52 and the image-processing unit 54 are formed to operate respectively in such a way that: the image pickup unit 52 receives while light reflected by an object 59 to be observed and plural types of fluorescence emitted from an aggregation 59a of fluorescent substances in the object 59; and the image-processing unit 54 outputs one frame of a white light image, one frame of the first fluorescence image, one frame of the white light image, and one frame of the second fluorescence image in chronological order every one rotation of the rotary filter 51b so that an output of the white light image is inserted between outputs of respective fluorescence images, with the result that a frame rate for the white light image is larger than frame rates for the respective fluorescence images.

SUMMARY OF THE INVENTION

A fluorescence endoscope apparatus according to the present invention is characterized in that the fluorescence endoscope apparatus includes: a light source unit that emits light in a combination of light in at least one of plural types of wavelength bands in two types of wavelength ranges of RGB and one of two types of exciting light, with plural types of emitting patterns and in a time division; an image pickup unit that receives light reflected by an object to be observed and two types of fluorescence emitted by two types of fluorescent substances that exist in the object by radiating to the object each light emitted from the light source unit in a time division; and an image-processing unit that outputs a white light image and two types of fluorescence images with the light that is received by the image pickup unit, and in that: the image pickup unit has three types of image-pickup ranges, receives the two types of fluorescence in a first image-pickup range, and receives reflected light in two types of wavelength bands and reflected light in a narrow wavelength band in a vicinity of the first image-pickup range in a second image-pickup range and in a third image-pickup range; and the image-processing unit outputs a first fluorescence image and a second fluorescence image with information on the two types of fluorescence that are received by the image pickup unit and outputs a pseudo white light image with information on the reflected light in the two types of the wavelength bands which is received by the image pickup unit and with information on the reflected light in the narrow band in the vicinity of the first image-pickup range which is received by the image pickup unit.

Also, in a fluorescence endoscope apparatus according to the present invention, it is preferred that the light source unit includes a diode light source that emits light in plural types of wavelength bands in the two types of wavelength ranges of RGB and the two types of exciting light separately.

Also, in a fluorescence endoscope apparatus according to the present invention, it is preferred that the light source unit includes: a light source that emits light containing white light and two types of exciting light; and a rotary filter that includes one or more pairs of a first transmittal portion and a second transmittal portion that are placed in the same circumferential direction, the first transmittal portion transmitting light in the two types of the wavelength bands in the two types of the wavelength ranges of RGB and the first exciting light out of the plural types of light emitted from the light source, the second transmittal portion transmitting light in the narrow band in the vicinity of the first image-pickup range and the second exciting light out of the plural types of light emitted from the light source, and the pairs of the transmittal portions being placed in the same circumferential direction.

Also, in a fluorescence endoscope apparatus according to the present invention, it is preferred that the image pickup unit includes a single-chip color image sensor and it is preferred that the image-processing unit includes: an image-capturing unit that converts an electrical signal of light received in each image-pickup range of the single-chip color image sensor, into image information with respect to each image-pickup range; a memory to which the converted image information with respect to each image-pickup range due to the image-capturing unit is written with respect to each emitting pattern;

an image-generating unit that generates and outputs a white light image and a fluorescence image with the image information with respect to each image-pickup region which is written to the memory for each emitting pattern; and a timing-controlling unit that controls timing with which the white light image and the fluorescence image are generated to be outputted in accordance with a rate at which the emitting patterns of the light source unit are switched to one another.

Also, in a fluorescence endoscope apparatus according to the present invention, it is preferred that the image pickup unit includes a three-chips image sensor and it is preferred that the image-processing unit includes: an image-capturing unit that converts an electrical signal of light received in each image-pickup range of the three-chips image sensor, into image information with respect to each image-pickup range; a memory to which the converted image information with respect to each image-pickup range due to the image-capturing unit is written with respect to each emitting pattern; an image-generating unit that generates and outputs a white light image and a fluorescence image with the image information with respect to each image-pickup region which is written to the memory for each emitting pattern; and a timing-controlling unit that controls timing with which the white light image and the fluorescence image are generated to be outputted in accordance with a rate at which the emitting patterns of the light source unit are switched to one another.

Also, in a fluorescence endoscope apparatus according to the present invention, it is preferred that: the image pickup unit receives the two types of fluorescence in the first image-pickup range; the image pickup unit receives reflected light in the first wavelength band out of the plural types of reflected light in the two types of wavelength bands, in the second image-pickup range; and the image pickup unit receives reflected light in the second wavelength band out of the plural types of reflected light in the two types of wavelength bands and reflected light in the narrow band in the vicinity of the first image-pickup range, in the third image-pickup range.

Also, in a fluorescence endoscope apparatus according to the present invention, it is preferred that: the image pickup unit is formed to receive light such that a wavelength of one of reflected light in the second wavelength band and reflected light in the narrow band in the vicinity of the first image-pickup range which are received in the third image-pickup range is longer than 600 nm and a wavelength of the other is shorter than 600 nm.

These and other features and advantages of the present invention will become apparent from the following detailed description of the preferred embodiments when taken in conjunction with the accompanying drawings.

BRIEF DESCRIPTION OF THE DRAWINGS

FIG. 1A is a block diagram conceptually showing its whole structure, FIG. 1B is a view showing a configuration of respective transmittal portions of a rotary filter that is provided for a light source unit for the apparatus shown in FIG. 1A, and FIG. 1C is a timing chart conceptually showing timing with which a white light image and plural types of fluorescence images are captured in the fluorescence endoscope apparatus disclosed in Japanese Patent Kokai No. 2011-188929.

FIG. 2A is a timing chart conceptually showing one example of timing with which a white light image and two types of fluorescence images are captures, in a fluorescence endoscope apparatus of a comparative example, FIG. 2B is a timing chart conceptually showing one example of timing with which a white light image and two types of fluorescence images are captures, in a fluorescence endoscope apparatus according to the present invention, and FIG. 2C is a timing chart conceptually showing another example of timing with which a white light image and two types of fluorescence images are captures, in the fluorescence endoscope apparatus according to the present invention.

FIG. 3A is a graph showing t absorption characteristics of oxyhemoglobin relative to wavelengths, FIG. 3B is a photograph of a blood vessel containing oxyhemoglobin which is an object to be observed, and FIGS. 3C to 3F are views conceptually showing images of the blood vessel containing oxyhemoglobin, the images being captured with different wavelengths respectively, FIG. 3C is a view showing an image captured with light in the wavelength range of B (400 nm to 470 nm), FIG. 3D is a view showing an image captured with light in the wavelength range of G (470 nm to 580 nm), FIG. 3E is a view showing an image captured with light with a wavelength shorter than 600 nm in the wavelength range of R (580 nm to 600 nm), and FIG. 3F is a view showing an image captured with light with a wavelength longer than 600 nm in the wavelength range of R (600 nm to 700 nm).

FIGS. 5A-5D are explanatory views showing optical characteristics of filters or the like which are used for the fluorescence endoscope apparatus of the first embodiment. To be specific, FIG. 5A shows wavelength-transmittance ranges of filters provided for a single-chip color image sensor and used for respective image-pickup ranges, FIG. 5B shows wavelength-transmittance bands of an exciting-light cut filter and the first and second fluorescence wavelength bands in which the first and second fluorescent substances emit fluorescence respectively, FIG. 5C shows wavelength bands in which illumination light is emitted with the first emitting pattern, and FIG. 5D shows wavelength bands in which illumination light is emitted with the second emitting pattern.

FIG. 6A shows one example of the timing chart, and FIG. 6B shows another example of the timing chart.

FIGS. 8A-8D are explanatory views showing optical characteristics of filters or the like which are used for the fluorescence endoscope apparatus of the second embodiment. To be specific, FIG. 8A shows wavelength-transmittance bands of respective image-pickup ranges of a three-chips image sensor, FIG. 8B shows wavelength-transmittance bands of an exciting-light cut filter and the first and second fluorescence wavelength bands in which the first and second fluorescent substances emit fluorescence respectively, FIG. 8C shows wavelength bands in which illumination light is emitted with the first emitting pattern, and FIG. 8D shows wavelength bands in which illumination light is emitted with the second emitting pattern.

FIG. 9A shows one example of the timing chart, and FIG. 9B shows another example of the timing chart.

FIGS. 10A-10B are explanatory views conceptually showing effects of a fluorescence endoscope apparatus of yet another embodiment according to the present invention in which the emitting patterns for the first embodiment are used in combination with the emitting patterns for the second embodiment. To be specific, FIG. 10A is a timing chart conceptually showing timing with which a white light image and four types of fluorescence images are captures, in a fluorescence endoscope apparatus of a comparative example, and FIG. 10B is a timing chart conceptually showing one example of timing with which a white light image and four types of fluorescence images are captures, in a fluorescence endoscope apparatus according to the present invention.

DETAILED DESCRIPTION OF THE PREFERRED EMBODIMENTS

Prior to explanations for the embodiments, operation effects of the present invention are explained.

A fluorescence endoscope apparatus according to the present invention includes: a light source unit that emits light in a combination of light in at least one of plural types of wavelength bands in two types of wavelength ranges of RGB and one of two types of exciting light, with plural types of emitting patterns and in a time division; an image pickup unit that receives light reflected by an object to be observed and two types of fluorescence emitted by two types of fluorescent substances that exist in the object by radiating to the object each light emitted from the light source unit in a time division; and an image-processing unit that outputs a white light image and two types of fluorescence images with the light that is received by the image pickup unit. The image pickup unit has three types of image-pickup ranges, receives the two types of fluorescence in a first image-pickup range, and receives reflected light in two types of wavelength bands and reflected light in a narrow wavelength band in a vicinity of the first image-pickup range in a second image-pickup range and in a third image-pickup range. And, the image-processing unit outputs a first fluorescence image and a second fluorescence image with information on the two types of fluorescence that are received by the image pickup unit and outputs a pseudo white light image with information on the reflected light in the two types of the wavelength bands which is received by the image pickup unit and with information on the reflected light in the narrow band in the vicinity of the first image-pickup range which is received by the image pickup unit.

That is to say, in the fluorescence endoscope apparatus of the present invention, pseudo color information on the first image-pickup range that is used for receiving fluorescence is acquired through the second or third image-pickup range next to the first image-pickup range used for receiving fluorescence, in one image pickup unit, and it is possible to output a white light image with the pseudo color information as acquired and with color information on two reflected light components that are captured through the second and third image-pickup ranges other than the first image-pickup range used for receiving fluorescence.

Such a manner makes it possible to use a process of one frame for capturing a white light image also for capturing a fluorescence image. As a result, it is possible to decrease the number of frames necessary for outputting two types of fluorescence images and a white light image by one frame, even though the fluorescence endoscope apparatus has a simple structure. In addition, it is possible to remarkably improve a frame rate for plural types of fluorescence images without deteriorating a frame rate for a white light image.

This respect is described below in detail using the drawings.

Figure 1A:
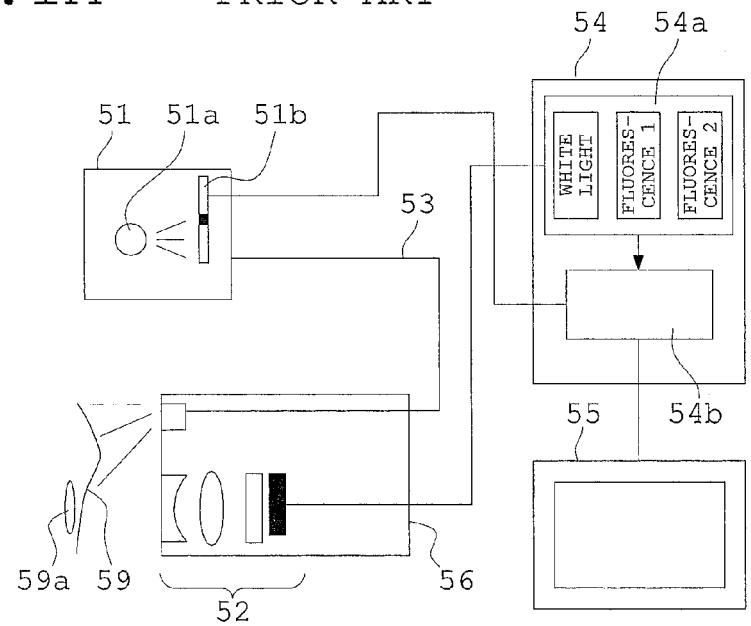
FIGS. 1A-1C are explanatory views showing one example of structures for the fluorescence endoscope apparatus disclosed in Japanese Patent Kokai No. 2011-188929. To be specific.
Figure 1B:
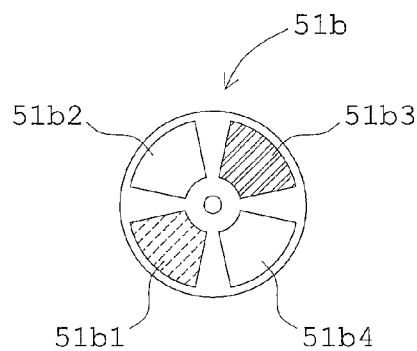
Figure 1C:
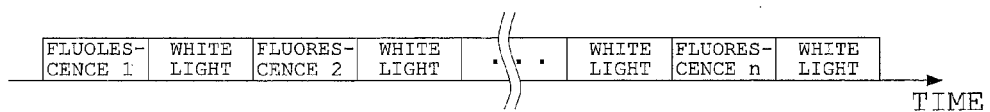
Figure 2A:
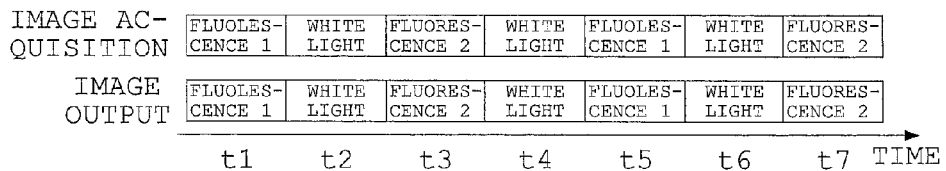
FIGS. 2A-2C are explanatory views conceptually showing effects of a fluorescence endoscope apparatus according to the present invention. To be specific.
Figure 2B:
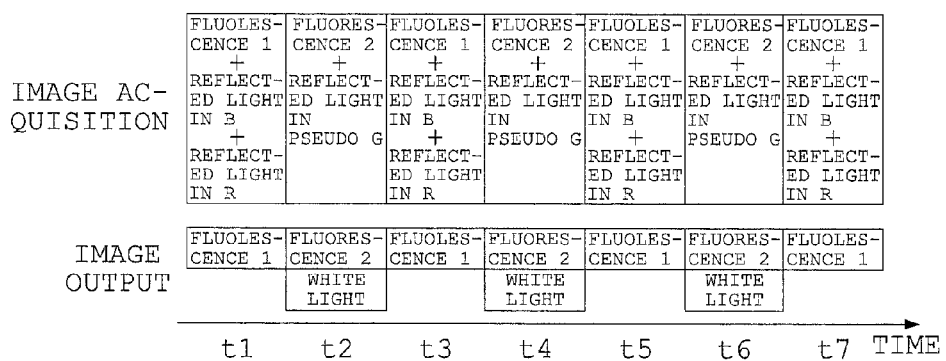
Figure 2C:
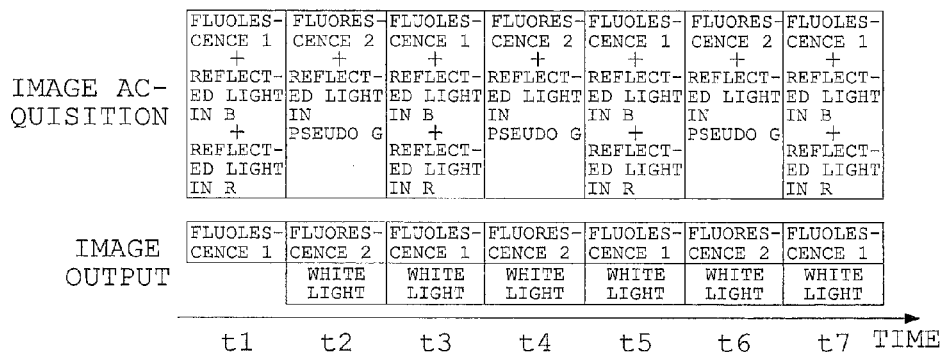

FIGS. 2A-2C are explanatory views conceptually showing effects of a fluorescence endoscope apparatus according to the present invention. To be specific, FIG. 2A is a timing chart conceptually showing one example of timing with which a white light image and two types of fluorescence images are captures, in a fluorescence endoscope apparatus of a comparative example, FIG. 2B is a timing chart conceptually showing one example of timing with which a white light image and two types of fluorescence images are captures, in a fluorescence endoscope apparatus according to the present invention, and FIG. 2C is a timing chart conceptually showing another example of timing with which a white light image and two types of fluorescence images are captures, in the fluorescence endoscope apparatus according to the present invention. Besides, a timing chart for an image-capturing process (that is a process ranging from image acquisition by the image sensor to storage into the frame memory) is shown on the upper side of each of FIGS. 2A, 2B, and 2C, and a timing chart for an image-outputting process (that is a process of generating and outputting an image with image information written to the frame memory) is shown on the lower side of each of FIGS. 2A, 2B, and 2C.

A fluorescence endoscope apparatus of a comparative example is formed to capture a white light image and fluorescence images to insert an output of a white light image between outputs of fluorescence images different from each other in type and to repeat outputs of images in such a manner with one image pickup unit, like the fluorescence endoscope apparatus disclosed in Japanese Patent Kokai No. 2011-188929 for example.

For example, in the case where a white light image and two types of fluorescence images are captured with the fluorescence endoscope apparatus of the comparative example, images are outputted repeatedly in the order of the first fluorescence image (fluorescence 1), the white light image, the second fluorescence image (fluorescence 2), and the white light image, as shown in FIG. 2A.

In this case, an image-outputting process of three frames is needed in order to output the two types of fluorescence images and the white light image.

And, the first fluorescence image (fluorescence 1) needs an image-outputting process of three frames for outputting the white light image, the second fluorescence image (fluorescence 2), and the white light image until the next output point t5 of time after outputting the first fluorescence image at a point t1 of time for example. Similarly, the second fluorescence image (fluorescence 2) needs an image-outputting process of three frames for outputting the white light image, the first fluorescence image (fluorescence 1), and the white light image until the next output point t7 of time after outputting the second fluorescence image at a point t3 of time for example.

On the other hand, an image-outputting process of one frame is sufficient for the white light image in order to output the first fluorescence image (fluorescence 1) (the second fluorescence image (fluorescence 2)) until the next output point t4 (t6) of time after outputting the white light image at a point t2 (t4) of time for example.

As described above, in the case of the fluorescence endoscope apparatus of the comparative example, a frame rate for the white light image can be kept high but frame rates for the plural types of the fluorescence images deteriorate because of an increase in the number of frames for the white light image the output of which is inserted between an output of one type of fluorescence image and the next output of the identical type of fluorescence image.

On the other hand, a fluorescence endoscope apparatus according to the present invention is formed to output images repeatedly with one image pickup unit in order of the first fluorescence image (fluorescence 1), and a white light image and the second fluorescence image (fluorescence 2), as shown in FIG. 2B for example.

Besides, in the example shown in FIG. 2B, it is presumed that reflected light that is in a predetermined wavelength band in the wavelength ranges of R and B and that has been captured in an output of the first fluorescence image (fluorescence 1) is combined with reflected light that is in the narrow wavelength band in the vicinity of the wavelength band of the second fluorescence and captured in an output of the second fluorescence image (fluorescence 2) so that the white light image and the second fluorescence image (fluorescence 2) are outputted at the same time.

In this case, an image-outputting process of two flames is sufficient to output the two types of fluorescence images and the white light image, and the number of frames decreases, as compared with the fluorescence endoscope apparatus of the comparative example shown in FIG. 2A.

And, an image-outputting process of one frame is sufficient for the first fluorescence image (fluorescence 1) in order to output the white light image and the second fluorescence image (fluorescence 2) until the next output point t3 of time after outputting the first fluorescence image at a point t1 of time for example. Similarly, an image-outputting process of one frame is sufficient for the second fluorescence image (fluorescence 2) in order to output the first fluorescence image (fluorescence 1) until the next output point t4 of time after outputting the second fluorescence image at a point t2 of time for example.

Also, an image-outputting process of one frame t3 (t5) is sufficient for the white light image in order to output the first fluorescence image (fluorescence 1) (the second fluorescence image (fluorescence 2)) until the next output point t4 (t6) of time after outputting the white light image at a point t2 (t4) of time for example.

As described above, the fluorescence endoscope apparatus according to the present invention shown in FIG. 2B makes it possible to decrease the number of frames for outputting the two types of fluorescence images and the white light image by one frame, as compared with the fluorescence endoscope apparatus of the comparative example shown in FIG. 2A, and makes it possible to remarkably decrease the number of frames necessary for outputting the other types of images between an output of each type of fluorescence image of the plural types of the fluorescence images and the next output of the identical type of fluorescence image. As a result, frame rates for the fluorescence images become high in the fluorescence endoscope apparatus of the present invention. On the other hand, a frame rate for the white light image is kept high, like the fluorescence endoscope apparatus of the comparative example shown in FIG. 2A.

As a result, the fluorescence endoscope apparatus according to the present invention shown in FIG. 2B makes it possible to remarkably improve frame rates for plural types of fluorescence images without deteriorating a frame rate for a white light image, in spite of its simple structure with one image pickup unit.

Besides, with respect to timing of output of white light image, although the white light image and the second fluorescence image (fluorescence 2) are outputted at the same time in the example shown in FIG. 2B, a fluorescence endoscope apparatus according to the present invention can also output a white light image both in outputting the first fluorescence image (fluorescence 1) and in outputting the second fluorescence image (fluorescence 2), as shown in FIG. 2C.

In the example shown in FIG. 2C, reflected light that is in a predetermined wavelength band in two types of the wavelength ranges of R, G, and B and has been captured in an output of the first fluorescence image (fluorescence 1) is combined with reflected light that is in the narrow wavelength band in the vicinity of the wavelength band of the second fluorescence and captured in an output of the second fluorescence image (fluorescence 2) so that the white light image and the second fluorescence image (fluorescence 2) are outputted at the same time. Not only that but the reflected light that is in the narrow wavelength band in the vicinity of the wavelength band of the second fluorescence and has been captured in an output of the second fluorescence image (fluorescence 2) is combined with reflected light that is in a predetermined wavelength band in two types of the wavelength ranges of R, G, and B and captured in the next output of the first fluorescence image (fluorescence 1) so that the white light image and the first fluorescence image (fluorescence 1) are outputted at the same time.

That is to say, in the fluorescence endoscope apparatus shown in FIG. 2C, reflected light having been captured in an output of another fluorescence image just before an output of one fluorescence image is combined with reflected light captured in the output of the one fluorescence image in every output of each of various types of fluorescence images so that a white light image is outputted.

The fluorescence endoscope apparatus of the example shown in FIG. 2C not only has an effect of remarkably improving frame rates for plural types of fluorescence images like the example shown in FIG. 2B but also can continue to output a white light image at all times, so that the example shown in FIG. 2C makes it possible to remarkably improve the frame rate for the white light image.

Also, in a fluorescence endoscope apparatus according to the present invention, it is preferred that the light source unit includes a diode light source that emits light in plural types of wavelength ranges in the two types of wavelength ranges of RGB and the two types of exciting light separately.

The fluorescence endoscope apparatus formed in such a manner does not need any rotary filter, so that it is possible to easily control time sharing of emitting patterns.

Alternatively, the light source unit may be formed to include: a light source that emits light containing white light and two types of exciting light; and a rotary filter that includes one or more pairs of first and second transmittal portions that are placed in the same circumferential direction, the first transmittal portion transmitting light in the two types of the wavelength bands in the two types of the wavelength ranges of R, G, and B and the first exciting light out of the plural types of light emitted from the light source, the second transmittal portion transmitting light in the narrow band in the vicinity of the first image-pickup range and the second exciting light out of the plural types of light emitted from the light source, and the pairs of the transmittal portions being placed in the same circumferential direction.

Such a manner makes it possible to control plural types of emitting patterns with one light source, in a time division.

Also, in a fluorescence endoscope apparatus according to the present invention, it is preferred that the image pickup unit includes a single-chip color image sensor and it is preferred that the image-processing unit includes: an image-capturing unit that converts an electrical signal of light received in each image-pickup range of the single-chip color image sensor, into image information with respect to each image-pickup range; a memory to which the converted image information with respect to each image-pickup range due to the image-capturing unit is written with respect to each emitting pattern; an image-generating unit that generates and outputs a white light image and a fluorescence image with the image information with respect to each image-pickup region which is written to the memory for each emitting pattern; and a timing-controlling unit that controls timing with which the white light image and the fluorescence image are generated to be outputted in accordance with a rate at which the emitting patterns of the light source unit are switched to one another.

Such a manner not only makes it possible to receive the two types of fluorescence in the first image-pickup range to output the first and second fluorescence images respectively with information on the respective two types of the received fluorescence but also makes it possible to receive reflected light in the two types of the wavelength bands and reflected light in the narrow band in the vicinity of the first image-pickup range, in the second and third image-pickup ranges, to output a pseudo white light image with information on all of these types of reflected light that are received, only by using one image pickup unit. As a result, it is possible to downsize an image pickup unit and it is possible to make the fluorescence endoscope apparatus with low costs.

Alternatively, the image pickup unit may be formed to include a three-chips image sensor and the image-processing unit may be formed to include: an image-capturing unit that converts an electrical signal of light received in each image-pickup range of the three-chips image sensor, into image information with respect to each image-pickup range; a memory to which the converted image information with respect to each image-pickup range due to the image-capturing unit is written with respect to each emitting pattern; an image-generating unit that generates and outputs a white light image and a fluorescence image with the image information with respect to each image-pickup region which is written to the memory for each emitting pattern; and a timing-controlling unit that controls timing with which the white light image and the fluorescence image are generated to be outputted in accordance with a rate at which the emitting patterns of the light source unit are switched to one another.

Such a manner not only makes it possible to receive the two types of fluorescence in the first image-pickup range to output the first and second fluorescence images respectively with information on the respective two types of the received fluorescence but also makes it possible to receive reflected light in the two types of the wavelength bands and reflected light in the narrow band in the vicinity of the first image-pickup range, in the second and third image-pickup ranges, to output a pseudo white light image with information on all of these types of reflected light that are received. In addition, it is possible to obtain images with high resolution and good color reproducibility, as compared with the case where a single-chip color image sensor of mosaic type is used.

Also, in a fluorescence endoscope apparatus according to the present invention, it is preferred that: the image pickup unit receives the two types of fluorescence in the first image-pickup range; the image pickup unit receives reflected light in the first wavelength band out of the plural types of reflected light in the two types of wavelength bands, in the second image-pickup range; and the image pickup unit receives reflected light in the second wavelength band out of the plural types of reflected light in the two types of wavelength bands and reflected light in the narrow band in the vicinity of the first image-pickup range, in the third image-pickup range.

Also, in a fluorescence endoscope apparatus according to the present invention in order to obtain a pseudo color information, it is preferred that: the image pickup unit is formed to receive light such that a wavelength of one of reflected light in the second wavelength band and reflected light in the narrow band in the vicinity of the first image-pickup range which are received in the third image-pickup range is longer than 600 nm and a wavelength of the other is shorter than 600 nm.

Such a manner makes a fluorescence endoscope apparatus particularly effective in observing a blood vessel existing in an object to be observed, for example. It is because: a main factor that affects a difference between wavelengths longer than 600 nm and wavelengths shorter than 600 nm in how images look like is oxyhemoglobin, in the case where a body cavity is observed using an endoscope; and the absorbance of oxyhemoglobin remarkably deteriorates in the range of wavelengths longer than 600 nm, so that a difference between wavelengths longer than 600 nm and wavelengths shorter than 600 nm in how images look like becomes large when an image of the object is captured.

This respect is described in detail in FIGS. 3A-3F.

Figure 3A:
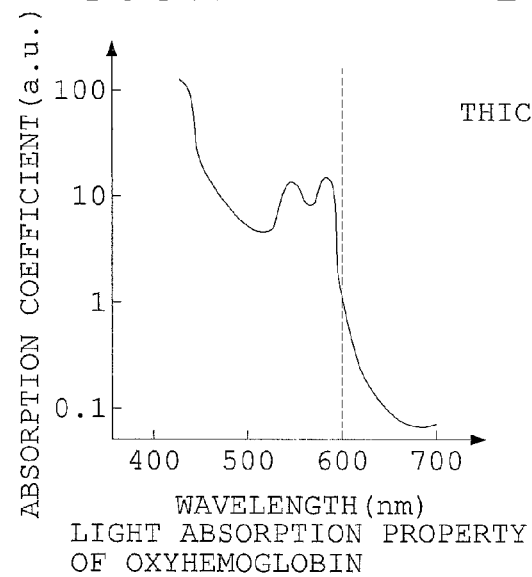
FIGS. 3A-3F are explanatory views showing the relation between absorbance of and an image of oxyhemoglobin with respect to each wavelength. To be specific.
Figure 3B:
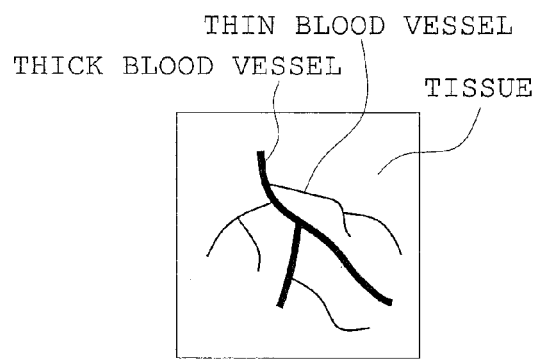
Figure 3C:
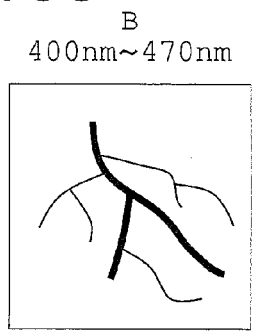
Figure 3D:
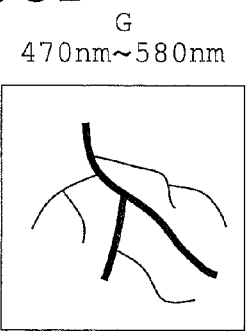
Figure 3E:
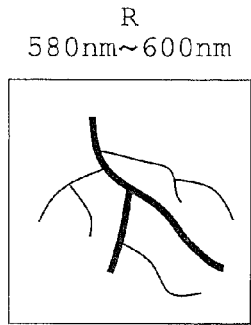
Figure 3F:
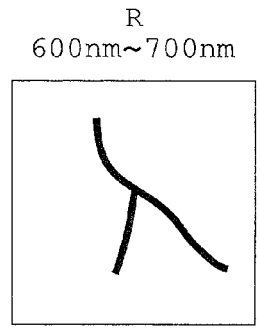

FIGS. 3A-3F are explanatory views showing the relation between absorbance of and an image of oxyhemoglobin with respect to each wavelength. To be specific, FIG. 3A is a graph showing absorption characteristics of oxyhemoglobin relative to wavelengths, FIG. 3B is a photograph of a blood vessel containing oxyhemoglobin which is an object to be observed, and FIGS. 3C to 3F are views conceptually showing images of the blood vessel containing oxyhemoglobin, the images being captured with different wavelengths respectively, FIG. 3C is a view showing an image captured with light in the wavelength range of B (400 nm to 470 nm), FIG. 3D is a view showing an image captured with light in the wavelength range of G (470 nm to 580 nm), FIG. 3E is a view showing an image captured with light with a wavelength shorter than 600 nm in the wavelength range of R (580 nm to 600 nm), and FIG. 3F is a view showing an image captured with light with a wavelength longer than 600 nm in the wavelength range of R (600 nm to 700 nm).

As shown in FIG. 3A, the absorbance of oxyhemoglobin sharply varies between wavelengths longer 600 nm and wavelengths shorter than 600 nm. That is to say, the absorbance of oxyhemoglobin is high in the range of wavelengths shorter than 600 nm but remarkably deteriorates in the range of wavelengths longer than 600 nm.

Accordingly, as shown in FIG. 3B for example, in the case where images of tissues containing blood vessels as an object to be observed are captured by emitting light with a wavelength of 400 nm to 470 nm, light with a wavelength of 470 nm to 580 nm, light with a wavelength of 580 nm to 600 nm, and light with a wavelength of 600 nm to 700 nm to the object respectively, the tissues can be observed with a high contrast between the blood vessels and the other tissues other than the blood vessels in an image in the case of using light with a wavelength of 600 nm or less because the absorbance of oxyhemoglobin in the blood vessels is high in the range of wavelengths of 600 nm or less and not only a thick blood vessel but also a thin blood vessel absorbs a large amount of light, as shown in FIGS. 3C to 3E. However, in the case of using light with a wavelength longer than 600 nm, the absorbance of oxyhemoglobin in the blood vessels is low in the range of wavelengths longer than 600 nm, so that only the thick blood vessel contrasts with the other tissues other than the thin blood vessel in an image as shown in FIG. 3F, the thin blood vessel absorbs an extremely small amount of light, and the thin blood vessel does not contrast with the other tissues other than the blood vessels in the image.

In this case, although wavelengths of 580 nm to 700 nm belong to the wavelength range of R, how blood vessels look like in an image varies between wavelengths longer than 600 nm and wavelengths shorter than 600 nm, as shown in FIGS. 3E and 3F.

For example, an image captured with light having a wavelength of 590 nm approximately looks like an image captured with light having a wavelength in the range of 470 nm to 580 nm.

Accordingly, the present inventor conceived a manner of capturing images with reflected light with a wavelength larger than 600 nm and an image with reflected light with a wavelength shorter than 600 nm with different timing from each other using one image-pickup range of three types of image-pickup ranges of an image pickup unit, so as to capture reflected light in another image-pickup range other than the one image-pickup range through the one image-pickup range in a pseudo manner.

As described above, in a fluorescence endoscope apparatus of the present invention which is formed so that: two types of fluorescence are received in the first image-pickup range; reflected light in the first wavelength band of plural types of reflected light in two types of wavelength bands is received in the second image-pickup range; and reflected light in the second wavelength band of the plural types of reflected light in the two types of wavelength bands and reflected light in the narrow band in the vicinity of the wavelength band of the second fluorescence are received in the third image-pickup range, an image pickup unit for the fluorescence endoscope apparatus is formed so that: one of the two types of the reflected light that are received in the third image-pickup range has a wavelength longer than 600 nm; and the other has a wavelength shorter than 600 nm, for example. As a result, even though these types of the reflected light received in the third image-pickup range are light in the wavelength range of 580 nm to 700 nm, or in the wavelength range of R, light with a wavelength shorter than 600 nm can be dealt with as a pseudo reflected light component in G. Besides, in the case where light in the wavelength range of 580 nm to 600 nm is dealt with as a pseudo reflected light component in G, it is preferred that light with a wavelength as near to the wavelength range in G as possible is used so that a white light image outputted with pseudo reflected light components in G approximates a white light image outputted with non-pseudo reflected light components in G, to the utmost.

Also, when the image pickup unit is formed so that: not only light in the wavelength range of 470 nm to 580 nm but also light in the wavelength range of 680 nm to 700 nm is received in the third image-pickup range; and one of the two types of the reflected light that are received in the third image-pickup range has a wavelength longer than 600 nm and the other has a wavelength shorter than 600 nm, for example, light the wavelength of which is longer than 600 nm and out of the fluorescence wavelength bands can be dealt with as a pseudo reflected light component in R. Besides, in the case where light the wavelength of which is longer than 600 nm and out of the fluorescence wavelength bands is dealt with a pseudo reflected light component in R, it is preferred that light with a wavelength as near to the wavelength range in R as possible is used so that a white light image outputted with the pseudo reflected light component in R approximates a white image outputted with a non-pseudo reflected light component in R to the utmost.

Such a manner makes: it possible to acquire pseudo color information on the first image-pickup range for receiving fluorescence with the second image-pickup range or the third image-pickup range next to the first image-pickup range for receiving fluorescence and two types of reflected light by acquiring the pseudo color information through the image pickup unit by using light in a narrow band with a wavelength slightly longer or shorter than a wavelength of light captured in the first image-pickup range for receiving fluorescence; and it possible to output a white light image with the acquired pseudo color information and two types of reflected light components captured in the second and third image-pickup ranges. Such a manner makes it possible to use also for capturing a fluorescence image an image-outputting process of one frame for capturing a white light image. As a result, it is possible to decrease the number of frames necessary for outputting two types of fluorescence images and a white light image, by one frame, in spite of its simple structure, and, in addition, it becomes possible to remarkably improve frame rates for plural types of fluorescence images without deteriorating a frame rate for a white light image.

Besides, in a fluorescence endoscope apparatus according to the present invention, combinations of a white light image and two types of fluorescence images are made so that at least one pair of the white light image and a fluorescence image is obtained. In the case where the number of combinations of the white light image and the two types of fluorescence images is increased, a frame rate for plural types of fluorescence images deteriorates the more. However, as described above, the present invention makes it possible to use also for capturing a fluorescence image an image-outputting process of one frame for capturing a white light image, so that the number of frames necessary for outputting plural types of fluorescence images and a white light image is decreased, as compared with the fluorescence endoscope apparatus of the comparative example, and frame rates for plural types of fluorescence images are remarkably improved.

First Embodiment

Figure 4:
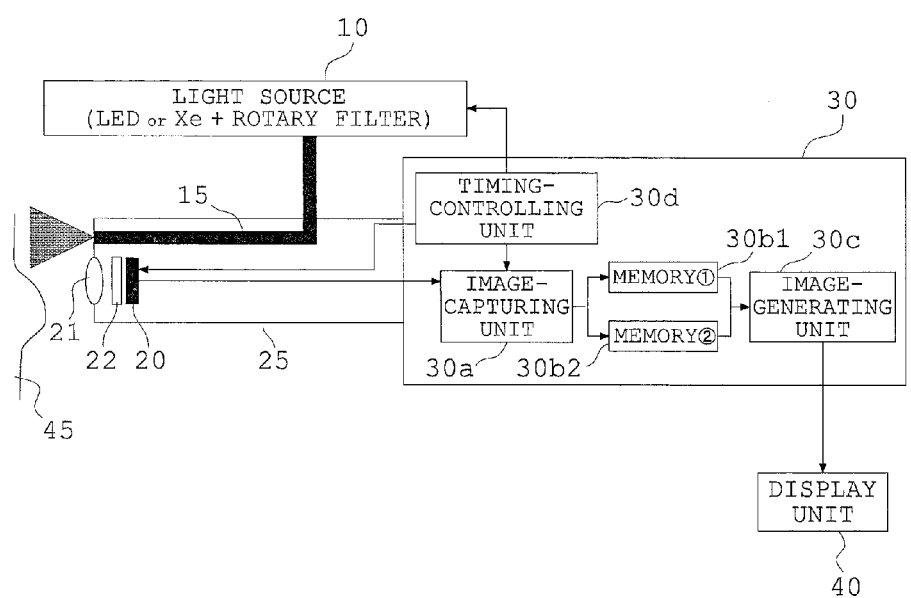
FIG. 4 is a block diagram schematically showing the whole structure of a fluorescence endoscope apparatus of a first embodiment according to the present invention.
Figure 6A:
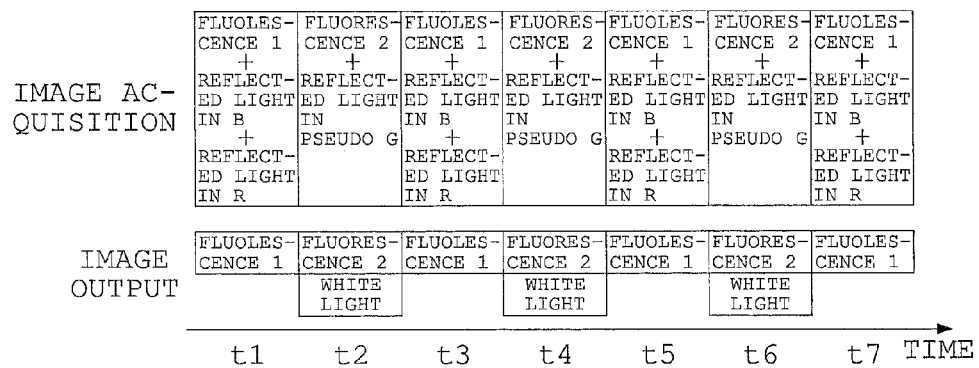
FIGS. 6A-6B are timing charts schematically showing timing with which a white light image and two types of fluorescence images are captured, in the fluorescence endoscope apparatus of the first embodiment. To be specific.
Figure 6B:
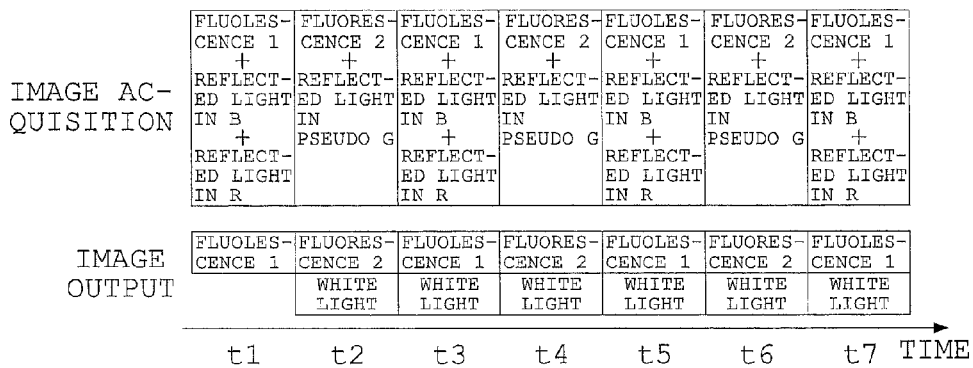

FIG. 4 is a block diagram schematically showing the whole structure of a fluorescence endoscope apparatus of a first embodiment according to the present invention. FIGS. 5A-5D are explanatory views showing optical characteristics of filters or the like which are used for the fluorescence endoscope apparatus of the first embodiment. To be specific, FIG. 5A shows wavelength-transmittance ranges of filters provided for a single-chip color image sensor and used for respective image-pickup ranges, FIG. 5B shows wavelength-transmittance bands of an exciting-light cut filter and the first and second fluorescence wavelength bands in which the first and second fluorescent substances emit fluorescence respectively, FIG. 5C shows wavelength bands in which illumination light is emitted with the first emitting pattern, and FIG. 5D shows wavelength bands in which illumination light is emitted with the second emitting pattern. FIGS. 6A-6B are timing charts conceptually showing timing with which a white light image and two types of fluorescence images are captured, in the fluorescence endoscope apparatus of the first embodiment. To be specific, FIG. 6A shows one example of the timing chart, and FIG. 6B shows another example of the timing chart.

Besides, it is presumed that a fluorescence endoscope apparatus of the first embodiment has a structure favorable for fluorescence observation in the case where a fluorescence substance which emits fluorescence in the wavelength range of 510 nm to 570 nm with a peak wavelength of 520 nm (corresponding to fluorescence 1 shown in FIG. 5B) is used as the first fluorescent substance and a fluorescence substance which emits fluorescence in the wavelength range of 520 nm to 580 nm with a peak wavelength of 550 nm (corresponding to fluorescence 2 shown in FIG. 5B) is used as the second fluorescent substance.

The fluorescence endoscope apparatus of the first embodiment is formed to include a light source unit 10, an image pickup unit 20, and an image-processing unit 30. Besides, in FIG. 4, the numeral reference 15 denotes a light-guiding means like a light guide, the numeral reference 25 denotes an endoscope insertion unit, the numeral reference 40 denotes a display unit of a display device, and the numeral reference 45 denotes an observed object which is a target to be observed.

The light source unit 10 emits light formed by combining light in at least one wavelength band of two types of wavelength bands in two types of wavelength ranges of R, G, and B with one exciting light of two types of exciting light, with plural types of emitting patterns and in a time division. Besides, for the sake of convenience, in this explanation, it is presumed that the first embodiment uses two types of emitting patterns.

In a detailed explanation about this matter, the light source unit 10 includes plural types of diode light sources like LED or LD which: emit light with a wavelength of 400 nm to 450 nm belonging to B, the first exciting light with a wavelength of 480 nm belonging to G, and light with a wavelength of 590 nm to 680 nm belonging to R separately from one another, in timing of the first emitting pattern, as shown in FIG. 5C; and emit the second exciting light with a wavelength of 500 nm belonging to G and light in a narrow wavelength band with a wavelength of 590 nm belonging to R separately from each other, in timing of the second emitting pattern, as shown in FIG. 5D.

Alternatively, the light source unit 10 may be formed to include: a light source like a Xe lamp which emits light with a wavelength of 400 nm to 700 nm; and a rotary filter which includes one or more pairs of first and second transmittal portions, the first and second transmittal portions being placed in the same circumferential direction, the first transmittal portion transmitting light with a wavelength of 400 nm to 450 nm belonging to B, the first exciting light with a wavelength of 480 nm belonging to G, and light with a wavelength of 590 nm to 680 nm belonging to R out of light emitted from the light source, the second transmittal portion transmitting the second exciting light with a wavelength of 500 nm belonging to G and light in a narrow wavelength band with its peak wavelength of 590 nm belonging to R out of the light emitted from the light source, and the pairs of the transmittal portions being placed in the same circumferential direction.

Besides, the intensities of light with a wavelength of 400 nm to 450 nm belonging to B, light with a wavelength of 590 nm to 680 nm belonging to R, and reflected light caused by emitting to the observed object 45 light in the narrow band with a wavelength of 590 nm belonging to R become much stronger, as compared with the intensity of fluorescence emitted from a fluorescent substance existing in the observed object 45 due to irradiation of exciting light. Accordingly, in the present invention, the intensity of light with a wavelength for reflected light which is emitted from the light source 10 is adjusted to become a predetermined weakened intensity, in order not to deteriorate an S/N ratio of a fluorescence signal due to the intensity of the reflected light, when the reflected light and fluorescence are captured simultaneously. Also, it is preferred that an observed object in which a fluorescent substance is located on its surface layer portions and fluorescence due to excitation by exciting light can be detected efficiently is used as a target to be observed, in a fluorescence endoscope apparatus according to the present invention.

The image pickup unit 20 is composed of a single-chip color image sensor. Besides, in FIG. 4, the numeral reference 21 denotes an objective lens, and the numeral reference 22 denotes an excitation cut filter.

The single-chip color image sensor 20 is formed so that color filters which have transmission characteristics corresponding to the respective wavelength ranges of R, G, and B (B: 400 nm to 470 nm, G: 470 nm to 580 nm, and R: 580 nm to 700 nm, in the example shown in FIG. 5A) respectively are placed on respective light-receiving elements respectively, for example, in a method of Bayer arrangement, so that the single-chip color image sensor 20 has three image-pickup ranges corresponding to the wavelength ranges of R, G, and B respectively due to the color filters having transmission characteristics different from one another respectively.

The image-processing unit 30 includes an image-capturing unit 30a, memories 30b1 and 30b2, an image-generating unit 30c, and a timing-controlling unit 30d.

The image-capturing unit 30a converts an electrical signal of light received in each of the image-pickup ranges of the single-chip color image sensor 20, into image information for each image-pickup range.

The memories 30b1 and 30b2 memorize image information for each image-pickup range into which the image-capturing unit 30a has converted the electrical signal, for each emitting pattern. In the example shown in FIGS. 5A-5D, the memory 30b1 memorizes image information on reflected light with a wavelength of 400 nm to 450 nm, image information on the first fluorescence in a wavelength range of 510 nm to 570 nm with a peak wavelength of 520 nm, and image information on reflected light with a wavelength of 590 nm to 680 nm, each image information being obtained by capturing images by the single-chip color image sensor 20 in the first emitting pattern to convert electric signals of the images by the image-capturing unit 30a respectively, as shown in FIG. 5C. Also, the memory 30b2 memorizes image information on the second fluorescence in a wavelength range of 520 nm to 580 nm with a peak wavelength of 550 nm and image information on reflected light in the narrow band with a wavelength of 590 nm, each image information being obtained by capturing images by the single-chip color image sensor 20 in the second emitting pattern to convert electric signals of the images by the image-capturing unit 30a respectively, as shown in FIG. 5D.

The image-generating unit 30c generates and outputs a white light image and a fluorescence image with the image information for each image-pickup range which is written to the memories 31b1 and 32b2 for each emitting pattern. In the example shown in FIGS. 5A-5D, the image-generating unit 30c generates and outputs a first fluorescence image with the image information on the first fluorescence. Also, the image-generating unit 30c generates and outputs a second fluorescence image with the image information on the second fluorescence. Also, the image-generating unit 30c generates and outputs a white light image with the image information on the reflected light with a wavelength of 400 nm to 450 nm, the image information on the reflected light with a wavelength of 590 nm to 680 nm, and the image information on the reflected light in the narrow band including a wavelength of 590 nm.

In this case, the image information on the reflected light in the narrow band containing a wavelength of 590 nm can imitate the image information on reflected light in the wavelength range of G. It is because the absorbance of oxyhemoglobin remarkably deteriorates in the range of wavelengths longer than 600 nm and a difference between wavelengths longer than 600 nm and wavelengths shorter than 600 nm in how images look like in capturing the images of the observed object becomes large, as described above. Accordingly, in the case where the wavelength of one of the two types of reflected light that are received in the third image-pickup range shown in FIG. 5A is longer than 600 nm and the wavelength of the other is shorter than 600 nm for example, it is possible to deal with light with a wavelength shorter than 600 nm as a pseudo reflected light component in G, even though these types of the reflected light are in the wavelength range of R of 580 nm to 700 nm.

The timing-controlling unit 30d is formed to control timing with which a white light image and a fluorescence image are generated to be outputted in accordance with a ratio at which the emitting patterns of the light source unit 10 are switched to one another.

In a detailed explanation of this matter, for example, the timing-controlling unit 30d controls timing for operating the light source unit 10, timing for operating the image pickup unit 20, and timing for the image-processing unit 30 so that: the image pickup unit 20 receives reflected light and the first fluorescence and the image processing unit 30 generates and outputs the first fluorescence image, with timing with which an emitting pattern of the light source unit 10 has been switched to the first emitting pattern; and the image pickup unit 20 receives reflected light and the second fluorescence and the image processing unit 30 generates and outputs the second fluorescence image and the white light image, with timing with which an emitting pattern of the light source unit 10 has been switched to the second emitting pattern.

Besides, with respect to timing with which the white light image is generated to be outputted in the image pickup unit 20 and the image-processing unit 30, the timing-controlling unit 30d may control timing for operating the light source 10, timing for operating the image pickup unit 20, and timing for operating the image-processing unit 30 so that the white light image is generated to be outputted with the image information on the reflected light at the present point of time and the image information on the reflected light at the point of time just before the image information at the present point of time, as often as the emitting patterns are switched to one another.

The display unit 40 of the display device displays the white light image and the fluorescence image that are generated to be outputted by the image-generating unit 30c. Besides, a method of displaying images by the display unit 40 may be a method of displaying a white light image and a fluorescence image on areas different from each other on the display unit 40 respectively with the white image and the fluorescence image arranged in parallel, or a method of displaying the white light image and the fluorescence image on a common display area of the display unit 40 with the white light image and the fluorescence image superimposed.

In the fluorescence endoscope apparatus of the first embodiment formed in such a manner, light corresponding to the first emitting pattern and light corresponding to the second emitting pattern are emitted from the light source unit 10 in turn in a time division. Light emitted from the light source unit 10 passes through the light-guiding means 15 to be irradiated to the observed object 45. Light reflected by the observed object 45 and the first fluorescence and the second fluorescence (fluorescence 1 and fluorescence 2 shown in FIG. 5B) that are respectively emitted from the first and second fluorescent substances existing in the observed object 45 pass through the objective lens 21, exciting light is cut by the excitation cut filter 22, and an image is captured by the single-chip color image sensor 20. Electrical signals of light received in each image-pickup range of the single-chip color image sensor 20 is converted into image information for each image-pickup range by the image-capturing unit 30a, and the image information into which the electric signal is converted is written to the memories 30b1 and 30b2 for each emitting pattern. The image-generating unit 30c generates and outputs a white light image and a fluorescence image with the image information for each image-pickup range that is written to the memories 31b1 and 31b2 for each emitting pattern.

In a detailed explanation of this matter, in the example shown in FIGS. 5A-5D, the image-generating unit 30c generates and outputs the first fluorescence image with the image information on the first fluorescence with timing corresponding to the first emitting pattern. Also, the image-generating unit 30c generates and outputs not only the second fluorescence image with the image information on the second fluorescence but also the white light image with: the image information on the reflected light with a wavelength of 400 nm to 450 nm and the image information on the reflected light with a wavelength of 590 nm to 680 nm which have been written to the memory 30b1 with the timing corresponding to the first emitting pattern; and the image information on the reflected light in the narrow band containing a wavelength of 590 nm which is written to the memory 30b2 with timing corresponding to the second emitting pattern, with the timing corresponding to the second emitting pattern.

The outputted images are displayed on the display unit 40 of the display device.

In the fluorescence endoscope apparatus of the first embodiment, pseudo color information relative to G is acquired in an image-pickup range (the third image-pickup range) next to the image-pickup range for receiving fluorescence (the first image-pickup range) by using light in a narrow band with a wavelength (590 nm) slightly longer than a wavelength (470 nm to 580 nm) of light that is captured in the first image-pickup range for receiving fluorescence by the image pickup unit 20, and a white light image is outputted with the acquired pseudo color information relative to G and the color information on two types of reflected light in B and R that are captured in the second and third image-pickup ranges, so that it is possible to output the white light image in the second and third image-pickup ranges other than the first image-pickup range for imaging fluorescence, and a process of one frame for capturing a white light image can be used also for capturing a fluorescence image. As a result, it is possible to decrease the number of frames necessary for outputting two types of fluorescence images and a white light image, by one frame, in spite of its simple structure, and, in addition, it is possible to remarkably improve frame rates for plural types of fluorescence images without deteriorating a frame rate for a white light image.

Second Embodiment

Figure 7:
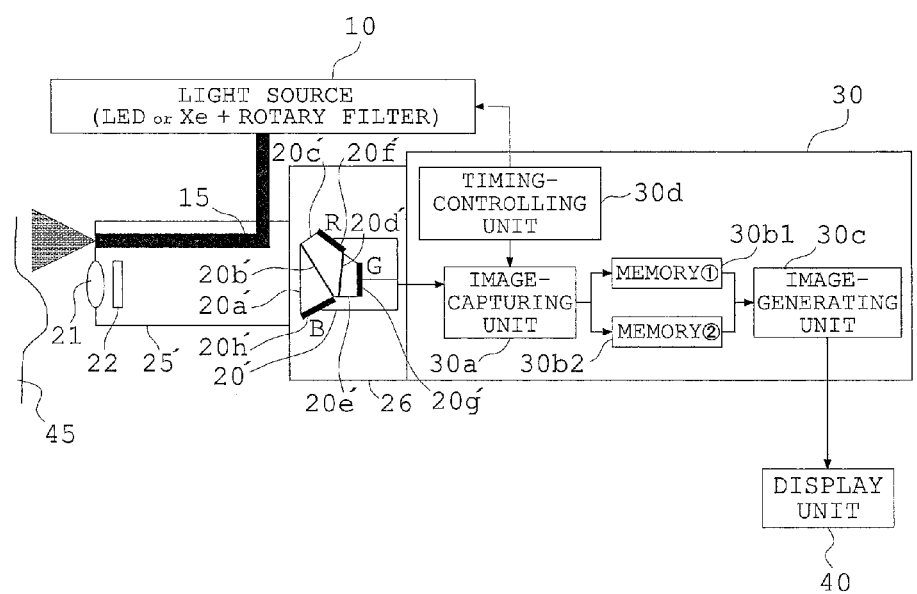
FIG. 7 is a block diagram conceptually showing the whole structure of a fluorescence endoscope apparatus of a second embodiment according to the present invention.
Figure 9A:
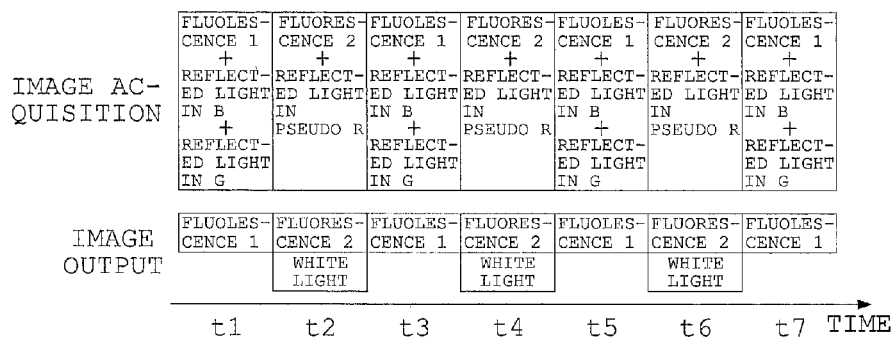
FIGS. 9A-9B are timing charts conceptually showing timing with which a white light image and two types of fluorescence images are captured, in the fluorescence endoscope apparatus of the second embodiment. To be specific.
Figure 9B:
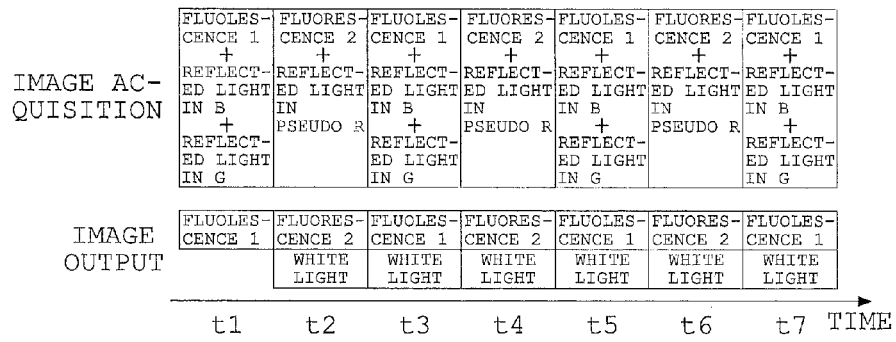

FIG. 7 is a block diagram schematically showing the whole structure of a fluorescence endoscope apparatus of a second embodiment according to the present invention. FIGS. 8A-8D are explanatory views showing optical characteristics of filters or the like which are used for the fluorescence endoscope apparatus of the second embodiment. To be specific, FIG. 8A shows wavelength-transmittance bands of respective image-pickup ranges of a three-chips image sensor, FIG. 8B shows wavelength-transmittance bands of an exciting-light cut filter and the first and second fluorescence wavelength bands in which the first and second fluorescent substances emit fluorescence respectively, FIG. 8C shows wavelength bands in which illumination light is emitted with the first emitting pattern, and FIG. 8D shows wavelength bands in which illumination light is emitted with the second emitting pattern. FIGS. 9A-9B are timing charts conceptually showing timing with which a white light image and two types of fluorescence images are captured, in the fluorescence endoscope apparatus of the second embodiment. To be specific, FIG. 9A shows one example of the timing chart, and FIG. 9B shows another example of the timing chart.

Besides, it is presumed that a fluorescence endoscope apparatus of the second embodiment has a structure favorable for fluorescence observation in the case where a fluorescence substance which emits fluorescence in the wavelength range of 590 nm to 640 nm with a peak wavelength of 610 nm (corresponding to fluorescence 1 shown in FIG. 8B) is used as the first fluorescent substance and a fluorescence substance which emits fluorescence in the wavelength range of 600 nm to 660 nm with a peak wavelength of 620 nm (corresponding to fluorescence 2 shown in FIG. 8B) is used as the second fluorescent substance.

The fluorescence endoscope apparatus of the second embodiment is formed to include the light source unit 10, an image pickup unit 20', and the image-processing unit 30. Besides, in FIG. 7, the numeral reference 25' denotes a rigid mirror insertion unit.

The light source unit 10 includes plural types of diode light sources like LED or LD which: emit light with a wavelength of 400 nm to 450 nm belonging to B, light with a wavelength of 500 nm to 540 nm belonging to G, and the first exciting light with a wavelength of 560 nm belonging to G separately from one another, in timing of the first emitting pattern, as shown in FIG. 8C; and emit the second exciting light with a wavelength of 570 nm belonging to G and light in a narrow wavelength band with a wavelength of 700 nm belonging to R separately from each other, in timing of the second emitting pattern, as shown in FIG. 8D.

Alternatively, the light source 10 may be formed to include: a light source like a Xe lamp which emits light with a wavelength of 400 nm to 700 nm; and a rotary filter which includes one or more pairs of first and second transmittal portions that are placed in the same circumferential direction, the first transmittal portion transmitting light with a wavelength of 400 nm to 450 nm belonging to B, light with a wavelength of 500 nm to 540 nm belonging to G, and the first exciting light with a wavelength of 560 nm belonging to G out of light emitted from the light source, the second transmittal portion transmitting the second exciting light with a wavelength of 570 nm belonging to G and light in a narrow wavelength band with its peak wavelength of 700 nm belonging to R out of the light emitted from the light source, and the pairs of the transmittal portions being placed in the same circumferential direction.

The image pickup unit 20' is composed of a three-chips image sensor. Besides, in FIG. 7, the numeral reference 26 denotes a camera head provided with the three-chips image sensor.

For example, the three-chips image sensor 20' is formed to include: a three colors-separating optical element including a first prism 20a', a blue light-reflecting dichroic mirror 20b' which reflects light in the wavelength range of B (400 nm to 470 nm) and transmits light in the wavelength ranges of G and R (470 nm to 580 nm, 580 nm to 700 nm), a second prism 20c', a red light-reflecting dichroic mirror 20d' which reflects light with a wavelength of 580 nm to 680 nm in the wavelength of R and transmits light in the wavelength ranges of G (470 nm to 580 nm) and light with a wavelength of 680 nm to 700 nm in the wavelength range of R, and a third prism 20e'; and image sensors 20f', 20g', and 20h' which correspond to the image-pickup ranges respectively and are placed on light-exit surfaces of the three colors-separating optical element respectively. The image sensor 20g' for the third image-pickup range captures an image, with light with a wavelength of 470 nm to 580 nm and light with a wavelength of 680 nm to 700 nm.

In the example shown in FIG. 8, the memory 30b1 memorizes: image information on reflected light with a wavelength of 400 nm to 450 nm, the image information being obtained by capturing images by the image sensor 20h' for the second image-pickup range in the first emitting pattern to convert electric signals of the images by the image-capturing unit 30a; image information on reflected light in a wavelength range of 500 nm to 540 nm, the image information being obtained by capturing images by the image sensor 20g' for the third image-pickup range in the first emitting pattern to convert electric signals of the images by the image-capturing unit 30a; and image information on the first fluorescence in a wavelength range of 590 nm to 640 nm with a peak wavelength of 610 nm, the image information being obtained by capturing images by the image sensor 20f' for the first image-pickup range in the first emitting pattern to convert electric signals of the images by the image-capturing unit 30a, as shown in FIG. 8C. Also, the memory 30b2 memorizes: image information on reflected light in the narrow band with a wavelength of 700 nm, the image information being obtained by capturing images by the image sensor 20g' for the third image-pickup range in the second emitting pattern to convert electric signals of the images by the image-capturing unit 30a; and image information on the second fluorescence in a wavelength range of 600 nm to 660 nm with a peak wavelength of 620 nm, the image information being obtained by capturing images by the image sensor 20f' for the first image-pickup range in the second emitting pattern to convert electric signals of the images by the image-capturing unit 30a, as shown in FIG. 8D.

The image-generating unit 30c generates and outputs a white light image and a fluorescence image with the image information for each image-pickup range which is written to the memories 31b1 and 32b2 for each emitting pattern. In the example shown in FIG. 8, the image-generating unit 30c generates and outputs a first fluorescence image with the image information on the first fluorescence. Also, the image-generating unit 30c generates and outputs a second fluorescence image with the image information on the second fluorescence. Also, the image-generating unit 30c generates and outputs a white light image with the image information on the reflected light with a wavelength of 400 nm to 450 nm, the image information on the reflected light with a wavelength of 500 nm to 540 nm, and the image information on the reflected light in the narrow band including a wavelength of 700 nm.

In this case, the image information on the reflected light in the narrow band containing a wavelength of 700 nm can imitate the image information on reflected light in the wavelength range of R, although the image sensor 20h' for the second image-pickup range captures an image with the reflected light in the narrow band containing a wavelength of 700 nm. It is because the absorbance of oxyhemoglobin remarkably deteriorates in the range of wavelengths longer than 600 nm and a difference between wavelengths longer than 600 nm and wavelengths shorter than 600 nm in how images look like in capturing images of the observed object becomes large, as described above. Accordingly, in the case where the wavelength of one of the two types of reflected light that are received in the third image-pickup range shown in FIG. 8A is longer than 600 nm and the wavelength of the other is shorter than 600 nm for example, it is possible to deal with light with a wavelength longer than 600 nm as a pseudo reflected light component in R, even though these types of the reflected light are light that is received in the third image-pickup range.

The other constitutions of the second embodiment are approximately the same as those of the first embodiment.

In the fluorescence endoscope apparatus of the second embodiment formed in such a manner, light corresponding to the first emitting pattern and light corresponding to the second emitting pattern are emitted from the light source unit 10 in turn in a time division. Light emitted from the light source unit 10 passes through the light-guiding means 15 to be irradiated to the observed object 45. Light reflected by the observed object 45 and plural types of fluorescence (fluorescence 1 and fluorescence 2 shown in FIG. 8B) that are respectively emitted from the first and second fluorescent substances existing in the observed object 45 pass through the objective lens 21, exciting light is cut by the excitation cut filter 22, and an image is captured by the three-chips image sensor 20'. An electrical signal of light received with each of the image sensors 20f', 20g', and 20h' for the image-pickup ranges of the three-chips image sensor 20' is converted into image information for each image-pickup range by the image-capturing unit 30a, and the image information into which the electric signal is converted is written to the memories 30b1 and 30b2 for each emitting pattern. The image-generating unit 30c generates and outputs a white light image and a fluorescence image with the image information for each image-pickup range that is written to the memories 31b1 and 31b2 for each emitting pattern.

In a detailed explanation of this matter, in the example shown in FIG. 8, the image-generating unit 30c generates and outputs the first fluorescence image with the image information on the first fluorescence with timing corresponding to the first emitting pattern. Also, the image-generating unit 30c generates and outputs not only the second fluorescence image with: the image information on the second fluorescence but also the white light image with the image information on the reflected light with a wavelength of 400 nm to 450 nm and the image information on the reflected light with a wavelength of 500 nm to 540 nm which have been written to the memory 30b1 with the timing corresponding to the first emitting pattern; and the image information on the reflected light in the narrow band containing a wavelength of 700 nm which is written to the memory 30b2 with timing corresponding to the second emitting pattern, with the timing corresponding to the second emitting pattern.

The outputted images are displayed on the display unit 40 of the display device.

In the fluorescence endoscope apparatus of the second embodiment, pseudo color information relative to R is acquired with an image-pickup range (the third image-pickup range) next to the image-pickup range for receiving fluorescence (the first image-pickup range) by using light in a narrow band with a wavelength (700 nm) slightly longer than a wavelength (580 nm to 680 nm) of light that is captured in the first image-pickup range for receiving fluorescence by the image pickup unit 20', and a white light image is outputted with the acquired pseudo color information relative to R and the color information on two types of reflected light in B and G that are captured in the second and third image-pickup ranges, so that it is possible to output the white light image with the second and third image-pickup ranges other than the first image-pickup range for imaging fluorescence, and a process of one frame for capturing a white light image can be used also for capturing a fluorescence image. As a result, it is possible to decrease the number of frames necessary for outputting two types of fluorescence images and a white light image, by one frame, in spite of its simple structure, and, in addition, it is possible to remarkably improve frame rates for plural types of fluorescence images without deteriorating a frame rate for a white light image.

Up to now, the fluorescence endoscope apparatuses of the embodiments according to the present invention have been explained. Fluorescence endoscope apparatus according to the present invention are not limited to the structures of the fluorescence endoscope apparatuses of these embodiments.

For example, in the present invention, the emitting patterns for the fluorescence endoscope apparatus of the first embodiment may be used in combination with the emitting patterns for the fluorescence endoscope apparatus of the second embodiment.

FIGS. 10A-10B are explanatory views conceptually showing effects of a fluorescence endoscope apparatus of yet another embodiment according to the present invention in which the emitting patterns for the first embodiment are used in combination with the emitting patterns for the second embodiment. To be specific, FIG. 10A is a timing chart conceptually showing timing with which a white light image and four types of fluorescence images are captures, in a fluorescence endoscope apparatus of a comparative example, and FIG. 10B is a timing chart conceptually showing one example of timing with which a white light image and four types of fluorescence images are captures, in a fluorescence endoscope apparatus according to the present invention.

Besides, in the example shown in FIG. 10, in order to distinguish the fluorescent substances and fluorescence used for fluorescence observation in the fluorescence endoscope apparatus of the first embodiment from the fluorescent substances and fluorescence used for fluorescence observation in the fluorescence endoscope apparatus of the second embodiment respectively, the fluorescence 1 emitted from the first fluorescent substance used for fluorescence observation in the second embodiment and the fluorescence 2 emitted from the second fluorescent substance used for fluorescence observation in the second embodiment are called fluorescence 3 emitted from a third fluorescent substance and fluorescence 4 emitted from a fourth fluorescent substance, respectively.

The fluorescence endoscope apparatus of the comparative example is formed to capture a white light image and fluorescence images with one image pickup unit and to output the white light image and the fluorescence images repeatedly in such a way that an output of the white light is inserted between outputs of fluorescence images different from each other in type, like the fluorescence endoscope apparatus disclosed in Japanese Patent Kokai No. 2011-188929 for example, as described above.

In the case where a white light image and four types of fluorescence images are captured with the fluorescence endoscope apparatus of the comparative example, as shown in FIG. 10A, a first fluorescence image (fluorescence 1), a white light image, a second fluorescence image (fluorescence 2), the white light image, a third fluorescence image (fluorescence 3), the white light image, a fourth fluorescence image (fluorescence 4), and the white light image are outputted in that order, repeatedly.

In this case, an image-outputting process of seven frames is needed in order to output the four types of fluorescence images and the white light image.

And, an image-outputting process of seven frames is needed in order to output the white light image, the second fluorescence image (fluorescence 2), the white light image, the third fluorescence image (fluorescence 3), the white light image, the fourth fluorescence image (fluorescence 4), and the white light image, until a point t9 of time at which the first fluorescence image (fluorescence 1) is next outputted after the first fluorescence image (fluorescence 1) is outputted at some point t1 of time for example. An image-outputting process of seven frames is needed until the next output point of time after an output point of time, also for the second fluorescence image (fluorescence 2), the third fluorescence image (fluorescence 3), and the fourth fluorescence image (fluorescence 4), as well as the first fluorescence image (fluorescence 1).

On the other hand, in the case of a fluorescence endoscope apparatus in which the emitting patterns for the first embodiment is used in combination with the emitting patterns for the second embodiment, as shown in FIG. 10B for example, a first fluorescence image (fluorescence 1), a white light image and a second fluorescence image (fluorescence 2), the white light image, a third fluorescence image (fluorescence 3), and the white light image and a fourth fluorescence image (fluorescence 4) are outputted in that order, repeatedly.

Besides, in the example shown in FIG. 10B, the white light image and each of the second fluorescence image (fluorescence 2) and fourth fluorescence image (fluorescence 4) are simultaneously outputted. In a more detailed explanation of this matter, the white light image is outputted by combining: reflected light that is in a predetermined wavelength band in the wavelength ranges of R and B and has been captured in an output of the first fluorescence image (fluorescence 1); and reflected light that is in a narrow band in the vicinity of the wavelength band of the second fluorescence and captured in an output of the second fluorescence image (fluorescence 2). Also, the white light image is outputted by combining: reflected light that is in a predetermined wavelength band in the wavelength ranges of B and G and has been captured in an output of the third fluorescence image (fluorescence 3); and reflected light that is in a narrow band in the vicinity of the wavelength band of the fourth fluorescence and captured in an output of the fourth fluorescence image (fluorescence 4).

In this case, an image-outputting process of four frames is sufficient to output four types of fluorescence images and a white light image, and it is possible to decrease the number of frames by three frames, as compared with the fluorescence endoscope apparatus of the comparative example shown in FIG. 10A.

And, an image-outputting process of three frames is sufficient to output the white image and the second fluorescence image (fluorescence 2), the third fluorescence image (fluorescence 3), and white light image and the fourth fluorescence image (fluorescence 4) until a point t5 of time at which the first fluorescence image (fluorescence 1) is next outputted after the first fluorescence image (fluorescence 1) is outputted at the some point t1 of time for example. An image-outputting process of three frames is sufficient for outputs of images until the next output point of time after an output point of time, also for the second fluorescence image (fluorescence 2), the third fluorescence image (fluorescence 3), and the fourth fluorescence image (fluorescence 4), as well as the first fluorescence image (fluorescence 1).

As described above, according to the fluorescence endoscope apparatus of the present invention, even in the case where the emitting patterns for the first embodiment is used in combination with the emitting patters for the second embodiment as shown in FIG. 10B, it is possible to decrease the number of frames necessary for outputting four types of fluorescence images and a white light image by three frames, as compared with the fluorescence endoscope apparatus of the comparative example shown in FIG. 10A. As a result, it is possible to greatly decrease the number of frames for outputting the other types of fluorescence images until the next output of one type of fluorescence image of the plural types of fluorescence images after an output of the one type of fluorescence image, so that their frame rates become high. On the other hand, a frame rate for a white light image is kept high, as in the case of the fluorescence endoscope apparatus of the comparative example shown in FIG. 10A.

Accordingly, the fluorescence endoscope apparatus of the present invention shown in FIG. 10B also makes it possible to remarkable improve frame rates for plural types of fluorescence images without deteriorating a frame rate for a white light image, in spite of its simple structure with one image pickup unit.

In addition, although the fluorescence endoscope apparatus of each of the embodiments according to the present invention is formed so that a wavelength of light in the narrow band in the vicinity of the wavelength band of the second fluorescence is longer than wavelengths in the wavelength bands of the second fluorescence emitting from the second fluorescent substance, a fluorescence endoscope apparatus according to the present invention may be formed so that a wavelength of light in the narrow band in the vicinity of the wavelength band of the second fluorescence is shorter than wavelengths in the wavelength bands of the second fluorescence emitting from the second fluorescent substance.

A fluorescence endoscope apparatus according to the present invention is useful for apparatuses which need acquisition of a white light image used for acquiring information on the shape of an object to be observed, like a living body, and acquisition of plural types of fluorescence images used for acquiring information on a degenerate site of the object, like a lesion in a living body.

What is claimed is:

1. A fluorescence endoscope apparatus comprising
a light source unit emitting light in a combination of light in at least one of plural types of wavelength bands in two types of wavelength ranges of RGB and one of two types of exciting light, with plural types of emitting patterns and in a time division,
an image pickup unit receiving light reflected by an object to be observed and two types of fluorescence emitted by two types of fluorescent substances that exist in the object by radiating to the object each light emitted from the light source unit in a time division, and
an image-processing unit outputting a white light image and two types of fluorescence images with the light that is received by the image pickup unit,
the image pickup unit having three types of image-pickup ranges, receiving the two types of fluorescence in a first image-pickup range, and receiving reflected light in two types of wavelength bands and reflected light in a narrow wavelength band in a vicinity of the first image-pickup range in a second image-pickup range and in a third image-pickup range, and
the image-processing unit outputting a first fluorescence image and a second fluorescence image with information on the two types of fluorescence which are received by the image pickup unit and outputting a pseudo white light image with information on the reflected light in the two types of the wavelength bands which is received by the image pickup unit and with information on the reflected light in the narrow band in the vicinity of the first image-pickup range which is received by the image pickup unit.

2. A fluorescence endoscope apparatus according to claim 1, wherein the light source unit includes a diode light source which emits light in plural types of wavelength bands in the two types of wavelength ranges of RGB and the two types of exciting light separately.

3. A fluorescence endoscope apparatus according to claim 1, wherein the light source unit comprises a light source emitting light containing white light and two types of exciting light, and a rotary filter including one or more pairs of a first transmittal portion and a second transmittal portion which are placed in the same circumferential direction, the first transmittal portion transmitting light in the two types of the wavelength bands in the two types of the wavelength ranges of RGB and the first exciting light out of the plural types of light emitted from the light source, the second transmittal portion transmitting light in the narrow band in the vicinity of the first image-pickup range and the second exciting light out of the plural types of light emitted from the light source, and the pairs of the transmittal portions being placed in the same circumferential direction.

4. A fluorescence endoscope apparatus according to claim 1, wherein the image pickup unit comprises a single-chip color image sensor, and the image-processing unit comprises an image-capturing unit which converts an electrical signal of light received in each image-pickup range of the single-chip color image sensor, into image information with respect to each image-pickup range, a memory to which the converted image information with respect to each image-pickup range due to the image-capturing unit is written with respect to each emitting pattern, an image-generating unit which generates and outputs a white light image and a fluorescence image with the image information with respect to each image-pickup region which is written to the memory for each emitting pattern, and a timing-controlling unit which controls timing with which the white light image and the fluorescence image are generated to be outputted in accordance with a rate at which the emitting patterns of the light source unit are switched to one another.

5. A fluorescence endoscope apparatus according to claim 1, wherein the image pickup unit comprises a three-chips image sensor, and the image-processing unit comprises an image-capturing unit which converts an electrical signal of light received in each image-pickup range of the three-chips image sensor, into image information with respect to each image-pickup range, a memory to which the converted image information with respect to each image-pickup range due to the image-capturing unit is written with respect to each emitting pattern, an image-generating unit which generates and outputs a white light image and a fluorescence image with the image information with respect to each image-pickup region which is written to the memory for each emitting pattern, and a timing-controlling unit which controls timing with which the white light image and the fluorescence image are generated to be outputted in accordance with a rate at which the emitting patterns of the light source unit are switched to one another.

6. A fluorescence endoscope apparatus according to claim 4, wherein the image pickup unit receives the two types of fluorescence in the first image-pickup range, the image pickup unit receives reflected light in the first wavelength band out of the plural types of reflected light in the two types of wavelength bands, in the second image-pickup range, and the image pickup unit receives reflected light in the second wavelength band out of the plural types of reflected light in the two types of wavelength bands and reflected light in the narrow band in the vicinity of the first image-pickup range, in the third image-pickup range.

7. A fluorescence endoscope apparatus according to claim 5, wherein the image pickup unit receives the two types of fluorescence in the first image-pickup range, the image pickup unit receives reflected light in the first wavelength band out of the plural types of reflected light in the two types of wavelength bands, in the second image-pickup range, and the image pickup unit receives reflected light in the second wavelength band out of the plural types of reflected light in the two types of wavelength bands and reflected light in the narrow band in the vicinity of the first image-pickup range, in the third image-pickup range.

8. A fluorescence endoscope apparatus according to claim 6, wherein, the image pickup unit is formed to receive light such that a wavelength of one of reflected light in the second wavelength band and reflected light in the narrow band in the vicinity of the first image-pickup range which are received in the third image-pickup range is longer than 600 nm and a wavelength of the other is shorter than 600 nm.

9. A fluorescence endoscope apparatus according to claim 7, wherein, the image pickup unit is formed to receive light such that a wavelength of one of reflected light in the second wavelength band and reflected light in the narrow band in the vicinity of the first image-pickup range which are received in the third image-pickup range is longer than 600 nm and a wavelength of the other is shorter than 600 nm.

* * * * *